(12) United States Patent
Udem et al.

(10) Patent No.: US 10,297,974 B2
(45) Date of Patent: May 21, 2019

(54) GENERATING LASER PULSES AND SPECTROSCOPY USING THE TEMPORAL TALBOT EFFECT

(71) Applicant: Max-Planck-Gesellschaft zur Foerderung der Wissenschaften e. V., Munich (DE)

(72) Inventors: Thomas Udem, Munich (DE); Akira Ozawa, Garching bei Munich (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 0 days.

(21) Appl. No.: 15/891,343

(22) Filed: Feb. 7, 2018

(65) Prior Publication Data
US 2018/0233877 A1 Aug. 16, 2018

(30) Foreign Application Priority Data
Feb. 13, 2017 (EP) ..................... 17000224

(51) Int. Cl.
*G01J 3/02* (2006.01)
*G01J 3/10* (2006.01)
(Continued)

(52) U.S. Cl.
CPC ........... *H01S 3/1121* (2013.01); *G01J 3/0218* (2013.01); *G01J 3/10* (2013.01); *G01J 3/4338* (2013.01);
(Continued)

(58) Field of Classification Search
CPC .. H01S 3/0057; H01S 3/0675; H01S 3/06791; H01S 3/1109; H01S 3/1112; H01S 3/1121
See application file for complete search history.

(56) References Cited

U.S. PATENT DOCUMENTS

2009/0003391 A1* 1/2009 Li .................. H01S 3/0675
372/6
2011/0286474 A1* 11/2011 Takenaga ............... A61B 18/22
372/3
(Continued)

OTHER PUBLICATIONS

Pudo, Dominik, Michal Depa, and Lawrence R. Chen. "Single and multiwavelength all-optical clock recovery in single-mode fiber using the temporal Talbot effect." Journal of Lightwave Technology 25.10 (2007): 2898-2903. (Year: 2007).*
(Continued)

*Primary Examiner* — Shawn Decenzo
(74) *Attorney, Agent, or Firm* — Caesar Rivise, PC

(57) ABSTRACT

A method of generating laser pulses (1) includes: creating a circulating light field in resonator device (11) having resonator length L and an intra-cavity dispersion and configured for supporting light field resonator modes, and generating a pulse train of laser pulses (1) by a mode-locking mechanism. Laser pulses (1) are generated with a repetition frequency and provide a frequency comb with carrier frequency $\omega_o$ and comb modes in frequency space. The intra-cavity dispersion is selected such that round trip phases $\phi$ have a dependency on frequency $\omega$ according to $$\phi(\omega) = \pi m\left(\sqrt{1 + 4\frac{\omega - \omega_0}{m\omega_r}} - 1\right) + \frac{L}{c}\omega_0$$

wherein m is an integer providing effective repetition rate ($m\omega_r$) in combination with mode spacing $\omega_r$ at optical carrier frequency ($\omega_o$), and the mode-locking mechanism provides a coupling of the resonator modes whereby frequency difference ($\Delta n = \omega_{n+1} - \omega_n$) between neighboring mode frequencies ($\omega_n$, $\omega_{n+1}$) is a linear function of mode
(Continued)

frequency number n. Furthermore, a spectroscopy method for investigating a sample, a laser pulse source apparatus and a spectroscopy apparatus are described.

16 Claims, 2 Drawing Sheets

(51) Int. Cl.

| | | |
|---|---|---|
| *G01J 3/28* | (2006.01) | |
| *G01J 9/04* | (2006.01) | |
| *H01S 3/00* | (2006.01) | |
| *H01S 3/11* | (2006.01) | |
| *G01J 3/433* | (2006.01) | |
| *G01N 21/39* | (2006.01) | |
| *H01S 3/067* | (2006.01) | |

(52) U.S. Cl.
CPC .............. *G01J 9/04* (2013.01); *G01N 21/39* (2013.01); *H01S 3/0057* (2013.01); *H01S 3/0675* (2013.01); *H01S 3/06791* (2013.01); *H01S 3/1109* (2013.01); *H01S 3/1112* (2013.01); *G01J 2003/282* (2013.01); *G01J 2003/4332* (2013.01); *G01N 2021/391* (2013.01); *G01N 2021/399* (2013.01); *G01N 2201/0697* (2013.01)

(56) References Cited

U.S. PATENT DOCUMENTS

| | | | | |
|---|---|---|---|---|
| 2015/0102240 A1* | 4/2015 | Zhu | ................... | G01N 21/39 |
| | | | | 250/565 |
| 2016/0248217 A1* | 8/2016 | Fermann | ............. | H01S 3/06712 |
| 2017/0025812 A1* | 1/2017 | Das | ................... | H01S 3/06791 |
| 2017/0363417 A1* | 12/2017 | Cui | ................... | G01B 11/007 |
| 2018/0102625 A1* | 4/2018 | Bres | ........................ | H01S 3/161 |
| 2018/0191125 A1* | 7/2018 | Myasnikov | ......... | H01S 3/06791 |
| 2019/0013639 A1* | 1/2019 | Peng | ................... | H01S 3/1118 |

OTHER PUBLICATIONS

Azana, Jose, and Miguel A. Muriel. "Technique for multiplying the repetition rates of periodic trains of pulses by means of a temporal self-imaging effect in chirped fiber gratings." Optics letters 24.23 (1999): 1672-1674. (Year: 1999).*
Azana et al. (1999). Temporal Talbot effect in fiber gratings and its applications. Applied optics, 38(32), 6700-6704.
Bernhardt et al. (2010). Cavity-enhanced dual-comb spectroscopy. Nature Photonics, 4(1), 55-57.
Cortes et al. (2016). Arbitrary control of the free spectral range of periodic optical frequency combs through linear energy-preserving time-frequency Talbot effects. In Photonics Conference (IPC), 2016 IEEE (pp. 162-163). IEEE.
Hofer et al. (1991). Mode locking with cross-phase and self-phase modulation. Optics letters, 16(7), 502-504.
Ideguchi et al. (2014). Adaptive real-time dual-comb spectroscopy. Nature communications, 5, 3375: 1-8.
Suzuki et al. (2010). Femtosecond ultrashort pulse generation by addition of positive material dispersion. Optics Express, 18(22), 23088-23094.
Teng et al. (2014). Talbot image of two-dimensional fractal grating. Optics Communications, 315, 103-107.
Udem et al. (2002). Optical frequency metrology. Nature, 416(6877), 233-237.
European Search Report from corresponding EP 17000224 dated Jul. 28, 2017.

* cited by examiner

GENERATING LASER PULSES AND SPECTROSCOPY USING THE TEMPORAL TALBOT EFFECT

CROSS-REFERENCE TO RELATED APPLICATIONS

This patent application claims the benefit under 35 U.S.C. § 119(a) of EP 17000224.0 filed Feb. 13, 2017, the contents of which application are incorporated herein by reference in their entirety for all purposes.

BACKGROUND OF THE INVENTION

The present invention relates to a method of generating a pulse train of laser pulses, in particular by mode-coupling of resonator modes of a laser resonator. Furthermore, the invention relates to a spectroscopy method for investigating a sample, using the pulse train of laser pulses. Furthermore, the invention relates to a laser pulse source apparatus and a spectroscopy apparatus including the laser pulse source apparatus. Applications of the invention are available e.g. in laser physics, in particular spectroscopy.

In the present specification, reference is made to the following prior art illustrating the technical background of the invention:
[1] Th. Udem et al. in "Nature" 416, 233 (2002);
[2] M. Hofer et al. in "Opt. Lett." 16, 502 (1991);
[3] T. Ideguchi et al. in "Nat. Commun." 5, 3375 (2014);
[4] B. Bernhardt et al. in "Nature photonics" 4, 55 (2010);
[5] S. Teng et al. in "Opt. Commun." 315, 103 (2014);
[6] J. Azaña et al. in "Appl. Opt." 38, 6700 (1999);
[7] T. Suzuki et al. in "Opt. Expr." 18, 23088 (2010).

Creating laser pulses by mode-coupling of resonator modes of a laser resonator is generally known. Conventional pulse lasers typically create a pulse train of laser pulses, which can be represented in frequency space as a frequency comb with equidistant comb modes, resulting from the temporal periodicity of the pulse train (e.g. [1]).

Pulse lasers creating frequency combs, like e.g. mode-locked fiber lasers [2] have numerous applications in laser physics, metrology, spectroscopy and/or attosecond pulse generation. In particular, dual-comb spectroscopy has been proposed [3, 4], wherein Fourier transform spectroscopy is conducted with two conventional frequency combs each having an equidistant mode spacing. A first frequency comb is transmitted through a sample and afterwards superimposed with a second frequency comb having a slightly different repetition rate compared with the first frequency comb. The first and second frequency combs interfere, so that beating signals in the radio frequency range are obtained, which can be measured with a photo diode, resulting in information on the interaction of the mode frequencies of the first frequency comb with the sample. Conventional dual-comb spectroscopy has disadvantages in terms of the required two separate frequency combs, the necessary stabilization thereof and the need for a so-called adaptive sampling of the photo diode signal. In particular, the application of the dual-comb spectroscopy is limited by a relative jitter of the combs.

The Talbot effect has been described for the first time in 1836 as a peculiar phenomenon observed in the near field of an optical grating. Summing over contributions of the individual rulings to the total field in the Fresnel approximation, a term of the form $$\exp\left(-\frac{ikl^2a^2}{2z}\right)$$

appears with the wave number k, the rulings numbered by l and spaced by a and the distance from the grating z. Summing over l generally yields a rather complex intensity distribution. Talbot noted though that this term reduces to $\exp(-i2\pi l^2)=1$ at a distance of $z=ka^2/4\pi$. The remaining terms add up to the intensity at z=0 provided that this intensity is periodic with a [5].

The same phenomenon can be observed in the time domain with a periodic pulse train signal that is subject to group velocity dispersion k" (where k" is the second derivative of k ($\omega$) vs frequency $\omega$) that provides the quadratic phase evolution (temporal Talbot effect). The pulses first spread out in time, and then reassemble after propagation the distance $t_r^2/(2\pi|k"|)$, where $t_r$ is the pulse repetition time [6, 7]. In the past, the temporal Talbot effect has been used for pulse compression outside the laser resonator only.

BRIEF SUMMARY OF THE INVENTION

The objective of the invention is to provide an improved method of generating a pulse train of laser pulses by mode-coupling of resonator modes of a laser resonator, being capable of avoiding limitations of conventional techniques. In particular, the pulse train of laser pulses is to be created as a frequency comb having new applications, e.g. in laser physics. Furthermore, the objective of the invention is to provide an improved spectroscopy method for investigating a sample, being capable of avoiding limitations of conventional techniques. In particular, the spectroscopy method is to be capable of avoiding the disadvantages of the conventional dual-comb spectroscopy. Further objectives of the invention are to provide a correspondingly improved laser pulse source apparatus and spectroscopy apparatus including the laser pulse source apparatus.

These objectives are solved with a method of generating a pulse train of laser pulses, a spectroscopy method, a laser pulse source apparatus and a spectroscopy apparatus comprising the features of the independent claims, respectively. Preferred embodiments and applications of the invention are defined in the dependent claims.

According to a first general aspect of the invention, the above objective is solved by a method of generating laser pulses, comprising the steps of creating a circulating light field in a resonator device (optical cavity) having a resonator length L and an intra-cavity dispersion and being configured for supporting a plurality of resonator modes of the light field, and generating a pulse train of the laser pulses by mode-locking, in particular by passive mode coupling, e.g. based on the Kerr effect, or by active mode coupling, e.g. using an intra-cavity modulator, wherein the laser pulses provide a frequency comb with a plurality of comb modes in frequency space.

According to the invention, the intra-cavity group velocity dispersion (intra-cavity resonator dispersion) of the resonator device is selected such that round trip phases $\phi$ (also called comb mode phases) of the frequency comb have a dependency on frequency $\omega$ according to $$\phi(\omega) = \pi m\left(\sqrt{1 + 4\frac{\omega - \omega_0}{m\omega_r}} - 1\right) + \frac{L}{c}\omega_0$$

wherein c is the speed of light, m is an integer that gives an effective repetition rate ($m\omega_r$) in combination with a mode spacing $\omega_r$ at the optical carrier frequency $\omega_o$. This dependency on frequency results in mode-locking, which provides coupling of the resonator modes such that the frequency difference ($\Delta_n=\omega_{n+1}-\omega_n$) between neighboring mode frequencies ($\omega_n$, $\omega_{n+1}$) of the frequency comb is a linear function of a mode frequency number n (so called Talbot frequency comb). The frequency difference between neighboring mode frequencies increases or decreases with increasing light frequency. Due to the temporal Talbot effect, the periodic pulse-shaped light field circulating in the resonator device disintegrates and revives with the effective repetition frequency ($m\omega_r$) of the laser pulses output from the resonator device. The Talbot frequency comb is created such that the comb mode spacing of neighboring comb modes is in the radiofrequency range. Advantageously, this facilitates applications of the invention in spectroscopy.

Contrary to the conventional applications of the temporal Talbot effect, the inventors have disclosed the temporal Talbot effect inside a laser resonator, i.e. the same behavior like with the spatial Talbot effect is obtained in time domain with a single pulse-shaped light field that is on a repetitive path in an optical cavity. In contrast to a free space pulse train, higher order dispersion is provided as will be shown below. While the conventional temporal Talbot effect outside the cavity results in phase shifts of the comb modes only, the dispersion within the resonator cavity causes phase shifts inducing frequency shifts of the comb modes. Advantageously, the invention provides a new laser mode locking state in which the pulse disperses quickly and then revives after an integer number of cavity round trips. This mechanism is based on the temporal Talbot effect within the resonator cavity and is obtained by setting the amount of intra-cavity dispersion. According to a particular advantage of the invention, with the mode-locking, e.g. the Kerr effect is employed to force the laser into this mode of operation, even when the cold cavity dispersion is not exactly matched. The inventors have shown that the mode spectrum of the pulse train generated according the invention is not equidistant but has a linearly changing (increasing or decreasing) mode spacing of neighboring comb modes with frequency with very high precision. Advantageously, the invention can be implemented with available mode-locking techniques being adapted for providing the above round trip phase $\phi$ ($\omega$).

According to a second general aspect of the invention, the above objective is solved by a spectroscopy method for obtaining a spectral response of a sample, wherein the laser pulses created according to the above first general aspect of the invention are used. The spectroscopy method comprises the steps of generating the pulse train of laser pulses represented by the Talbot frequency comb, applying the laser pulses on the sample under investigation, detecting the laser pulses after the interaction with the sample with a detector device, and analyzing a detector signal of the detector device in a frequency range where beat frequencies of the resonator modes occur, in particular in the radio frequency range, for providing beat signals created by the comb modes of the pulse train of laser pulses. The spectral response of the sample is obtained from the beat signals. Advantageously, the Talbot frequency comb is self-referenced. The beating with the adjacent modes uniquely defines the optical mode frequency, which means that the optical spectrum is directly mapped into the beating frequency range in the radio frequency domain. Contrary to the dual frequency comb spectroscopy, the inventive spectroscopy method can be conducted with a single laser source apparatus creating the Talbot frequency comb. Particular measures for stabilizing two laser sources can be avoided. In particular, due to the use of one single laser source apparatus, the disadvantage of dual frequency comb spectroscopy resulting from the relative jitter of the combs is completely eliminated. Preferably, the detector device comprises at least one photodiode, having advantages in terms of high sensitivity and low costs.

According to a third general aspect of the invention, the above objective is solved by a laser pulse source apparatus, being configured for generating laser pulses, preferably according to the method of generating laser pulses of the above first general aspect of the invention. The laser pulse source apparatus comprises a resonator device having a resonator length and an intra-cavity dispersion and being configured for supporting a plurality of resonator modes of a circulating light field, wherein a mode locking mechanism is adapted for generating the laser pulses providing a frequency comb with carrier frequency $\omega_o$ and a plurality of comb modes in frequency space. According to the invention, the intra-cavity dispersion of the resonator device is selected such that round trip phases have the above dependency on frequency as mentioned with reference to the first general aspect of the invention. The mode locking mechanism is arranged for providing a coupling of the resonator modes such that the frequency difference ($\Delta_n=\omega_{n+1}-\omega_n$) between neighboring comb frequencies ($\omega_n$, $\omega_{n+1}$) is a linear function of a mode frequency number n.

Advantageously, the resonator device is a resonator of any laser device, e.g. a linear resonator or a ring resonator, having a dispersion such that the round trip phases have the above frequency dependency, like e.g. the resonator of a fiber laser. Preferably, the resonator device has a size (in particular single resonator circulation length) such that the comb mode spacing of neighboring comb modes is in the radiofrequency range. Using a fiber-laser-based design of the resonator device has advantages in terms of the small mode-volume and long interaction length. Furthermore, the fiber-laser is capable of introducing strong nonlinear effects such as nonlinear polarization rotation which is often used for conventional mode-locked fiber lasers (see e.g. [2]).

According to a fourth general aspect of the invention, the above objective is solved by a spectroscopy apparatus being configured for obtaining a spectral response of a sample under investigation, comprising a laser pulse source apparatus according to the above third general aspect of the invention, a sample holder being arranged for accommodating the sample and applying the laser pulses on the sample, a detector device being adapted for detecting the laser pulses after an interaction with the sample, a spectrum analyser device being adapted for analyzing a detector signal of the detector device for obtaining beat signals created by the comb modes of the pulse train of laser pulses, and a calculation device being adapted for determining the spectral response of the sample from the beat signals. Advantageously, the interaction of the laser pulses with the sample causes a variation of comb mode amplitudes, e.g. due to light frequency (wavelength) dependent absorption by the sample, resulting in a specific change of the beat signals of comb modes compared with the situation without an interaction with the sample. The beat signals are obtained by beating the comb modes with spectrally changing mode separation within the single Talbot frequency comb. Thus, the spectroscopy method can be implemented with one single laser pulse source apparatus rather than with two sources of conventional dual-comb spectroscopy, so that the disadvantages of the conventional technique are avoided.

According to a preferred embodiment of the invention, the intra-cavity dispersion is adjusted such that the mode frequency ($\omega_n$) with the mode frequency number n is given by $\omega_n = \omega_0 + (n + n^2/m)\omega_r$, wherein $\omega_o$ is a carrier frequency of the frequency comb. Particularly preferred, the intra-cavity dispersion is selected such that the k-th derivative of the round trip phase at the carrier frequency ($\omega_o$) is given by $$\phi_{\omega_0}^{(k)} = (-1)^{k+1} \frac{2^k(2k-3)!!\pi}{m^{k-1}\omega_r^k}$$

wherein k is the order of intra-cavity dispersion.

According to a further preferred embodiment of the invention, the frequency difference between neighboring comb frequencies ($\Delta_n = \omega_{n+1} - \omega_n$) is in the radio frequency (rf) range, in particular in the range from 50 MHz to 150 MHz. Advantageously, this facilitates an evaluation of the detector signal and provision of the sample spectrum. The rf signal is uniquely assigned to specific comb modes, e.g. with $\omega_r = 2\pi*100$ MHz and m=1,000,000 the beating between the Talbot comb modes with numbers 1 and 2 is at 100.0003 MHz, the one between modes 2 and 3 at 100.0005 MHz and so on. Each radio frequency belongs to one comb mode, thus allowing a direct measurement of spectrally resolved comb mode absorption in the sample.

Advantageously, multiple techniques are available for adjusting the intra-cavity dispersion in the resonator device. According to a preferred variant, particularly preferred using a fiber laser as the laser pulse source apparatus, the dispersion is set with at least one fiber Bragg grating (FBG). This variant has particular advantages in terms of easy setting a large amount of dispersion. Furthermore, the FBG easily can be integrated in a fiber ring laser or alternatively in the volume material of a bulk laser resonator. According to further, additional or alternative adjusting techniques, at least one intracavity prism and/or at least one intracavity grating included in the resonator device is used for setting the intra-cavity dispersion. Additionally or alternatively, the dispersion can be adjusted or at least subjected to fine-tuning by setting a temperature of the resonator device, e.g. via external temperature adjustment and/or via resonator pump power.

According to a preferred embodiment of the inventive spectroscopy method, a reference portion of the pulse train of laser pulses is detected, wherein the reference portion is a portion of the same Talbot frequency comb like the comb applied to the sample, but the reference portion is not influenced by an interaction with the sample. Preferably, the reference portion is obtained with a beam splitting device being arranged for splitting the output of the common laser pulse source device. A reference detector signal of the detector device is analyzed for obtaining reference beat signals created by the comb modes of the reference portion of the pulse train of laser pulses. The spectral response of the sample is determined from the beat signals and the reference beat signals. Advantageously, the reference beat signals allow a correction of eventual comb mode amplitude fluctuation occurring in the Talbot comb.

BRIEF DESCRIPTION OF THE DRAWINGS

Further details and advantages of the invention are described in the following with reference to the attached drawings, which show in.

DETAILED DESCRIPTION OF PREFERRED EMBODIMENTS

Features of the invention are described in the following with particular reference to the creation of the Talbot frequency comb using a fiber ring laser. The invention is not restricted to this embodiment but rather can be implemented with other types of laser resonators. Details of designing and operating the laser resonator are not described as far as they are known as such from prior art.

Figure 1:
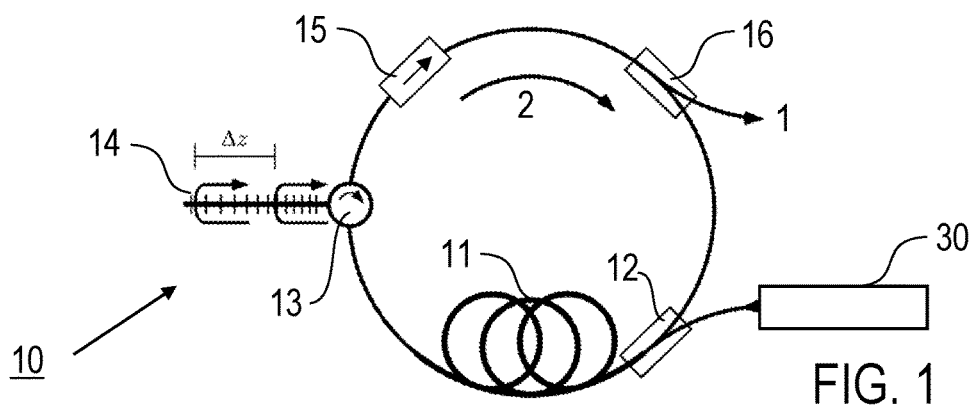
FIG. 1: a schematic illustration of a laser pulse source device according to a preferred embodiment of the invention.

According to the embodiment of FIG. 1, the laser pulse source apparatus 10 for generating and outputting laser pulses 1 comprises a fiber ring laser. The resonator device (resonator cavity) of the laser pulse source apparatus 10 is provided by a ring of an optical fiber (gain fiber), including a pump light combiner 12, in particular a wavelength division multiplexer (WDM), a circulator 13, a fiber Bragg grating section (FBG section) 14, an optical isolator 15 and an output coupler 16. The pump light combiner 12 is arranged for coupling pump light from a pump source 30 into the fiber and creating a circulating light field 2. With the circulator 13, the FBG section 14 is coupled with the fiber for adjusting the intra-cavity dispersion of the laser pulse source apparatus 10. For smaller values m and hence larger dispersion, several, e.g. two three or more FBG sections can be included via one or more circulators in the resonator device. The fiber comprises a gain material, like e.g. Ytterbium or Erbium doped fiber material. A mode-locking mechanism, e.g. based on nonlinear effects such as nonlinear polarization rotation or based on Kerr mode-locking is provided by the fiber and the FBG section 14 for coupling resonator modes such that the laser pulses 1 represent a frequency comb as described below. The output coupler 16 is arranged for coupling laser pulses 1 light out of the resonator device (fiber) 11, e.g. for an application in a spectroscopy apparatus 20 (see FIG. 2).

In the case of Talbot frequency comb, the mode-locking mechanism is effectively m times smaller than the conventional lasers. Therefore either strong nonlinear effects or matching the required dispersion (equation (6)) (see below) with higher fidelity (compared with conventional frequency combs) is provided to enforce mode-locking in the Talbot frequency comb. Intra-cavity dispersion is introduced through the FBG section 14 that can be designed with very large values for the group velocity dispersion and precise values for the higher order dispersions. To manufacture the FBG section 14, a photo sensitive fiber may be directly written with a UV laser. Up to the 6th order dispersion is commercially available.

Figure 2:
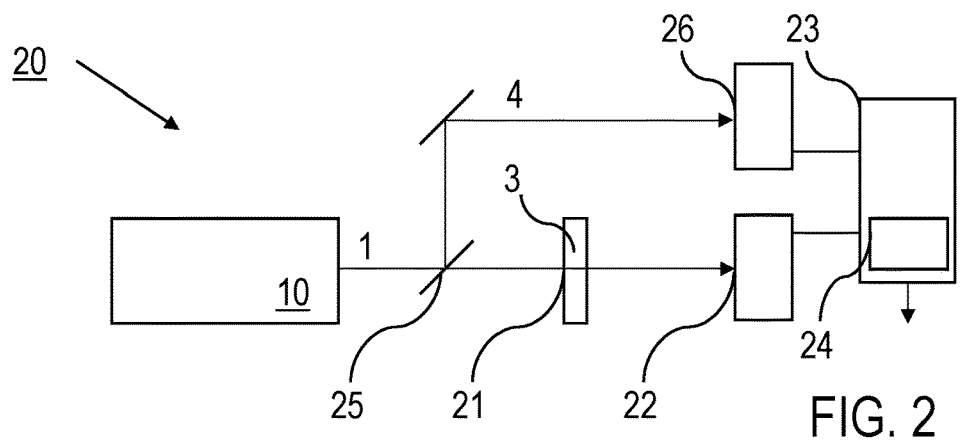
FIG. 2: a schematic illustration of a spectroscopy apparatus according to a preferred embodiment of the invention

According to the embodiment of FIG. 2, the spectroscopy apparatus 20 includes the inventive laser pulse source apparatus 10, e.g. according to FIG. 1, a sample holder 21 for accommodating the sample 3, a detector device 22 for detecting the laser pulses 1 after an interaction with the sample, a spectrum analyzer device 23 for analyzing a detector signal of the detector device 22 and for obtaining beat signals created by the comb modes of the pulse train of laser pulses 1, and a calculation device 24 for determining the spectral response of the sample 3 from the beat signals. Analyzing the beat signals can be implemented as known from conventional dual-comb spectroscopy. The calculation device 24 can be included in the spectrum analyzer device 23 and/or a main control device (not shown) of the spectroscopy apparatus. The sample holder 21 comprises e.g. a gas cell for the investigation of gaseous samples, a cuvette for accommodating liquid samples or a support platform for solid samples. The spectrometer geometry can be designed for a transmission or reflection measurement. The detector device 22 comprises a photodiode.

Between the laser pulse source apparatus 10 and the sample holder 21, a beam splitter 25 is optionally arranged. The beam splitter 25 directs a portion of the laser pulses 1 as reference light 4 to a reference detector device 26, which comprises another photodiode. Preferably, the detector devices 22, 26 have the same type of detectors and the same operations conditions. Detector signals from the reference detector device 26 are received by the spectrum analyzer device 23 for obtaining reference beat signals created by the comb modes of the pulse train of laser pulses 1 without an interaction with the sample 3. Comparing the reference beat signals with the beat signals in the detector signal from detector device 22 allow the correction of comb mode amplitude fluctuations.

In the following, creating the Talbot frequency comb by mode-locking of the resonator modes of the laser pulse source apparatus 10 is described. Mode-locking is provided by adjusting an intra-cavity dispersion such that the modes of the resonator cavity have a mode spectrum e.g. according to $$\omega_n = \omega_0 + \left(n + \frac{n^2}{m}\right)\omega_r \quad (1)$$

Here, the modes are numbered around the optical carrier frequency $\omega_0$ with integers $n = \pm 1, \pm 2, \pm 3, \ldots$ and $\omega_r$ is the mode spacing at the optical carrier frequency ($\omega_o$).

Contrary to the conventional regularly spaced frequency comb [1], there is a quadratic term in n which leads to a non-equally spaced comb of RF modes (comb with linearly changing spacing) with mode spacing as follows:

$$\Delta_n = \omega_{n+1} - \omega_n = \omega_r\left(1 + \frac{2n+1}{m}\right) \quad (2)$$

Since m is assumed to be much larger than 1 the mode spacings between the upper and lower modes relative to the optical carrier frequency $\omega_o$ are approximately $\omega_r$ (or an average of spacing to higher and lower mode). These RF modes are the result of beating between adjacent optical modes and can be seen in the power spectrum of the laser output. Higher order mode beatings like $\omega_{n+2} - \omega_n$ etc. are separated in the power spectrum by $\omega_r$.

This is similar to the harmonics of the repetition rate in a conventional frequency comb. The mode spacing at the carrier frequency $\omega_0$ is given approximately by $\omega_r$ for large m. It becomes the spacing for all modes for m→∞ for which (1) turns into a conventional frequency comb [1].

However, neither $\omega_r$ nor $\omega_0$ are the usual repetition frequency and offset frequency. Nevertheless they can be measured in very much the same way as for a regular frequency comb (see self-referencing, described below). Besides representing an all new mode locking regime, the interesting aspect of (1) is that each mode beating uniquely belongs to one particular pair of modes. For example the RF signal at $\omega_r$ (1+1/m) belongs to the beating between $\omega_0$ and $\omega_1$ and so on. Hence an RF spectrum recorded with a photo detector, e.g. 22 in FIG. 2, and a radio frequency spectrum analyzer, e.g. 23 in FIG. 2, directly displays a scaled down version of the optical spectrum of the laser pulse source apparatus 10.

By placing a sample 3 between the laser pulse source apparatus 10 and the detector device 22 and recording the change of the RF spectrum one gets the absorption spectrum of the sample 3. This is similar to a dual frequency comb setting with a linearly increasing spacing between the modes of the two frequency combs [3, 4], albeit with a single laser avoiding problems due to the relative jitter of the combs.

Depending on the magnitude of m, the mode spacing nominally becomes negative for n<−m/2. Physically this means that the corresponding spectral region possesses a negative group velocity. While this is possible in principle, this is excluded in practical applications of the invention, in particular for obtaining a reasonable laser design. Accordingly, preferably, it is assumed that the active modes (modes contributing to the gain) of the laser are limited to n>−m/2.

To see how the laser spectrum are forced to the modes defined by equation (1), the electric field E(t), e.g. 2 in FIG. 1, at a fixed point inside the cavity is computed as follows. Assuming that the modes oscillate with some complex amplitudes $a_n$, E(t) is obtained according to:

$$E(T) = E_o e^{-i\omega_0 t} \sum_{n=-\infty}^{+\infty} a_n e^{-i\left(n + \frac{n^2}{m}\right)\omega_r t} \quad (3)$$

Generally, this cannot represent a stable pulse in the time domain. However, assuming that m is an exact integer, the pulse will revive up to a phase factor after the time T $$E(t+T) = E_o e^{-i\omega_0(t+T)} \sum_n a_n e^{-i\left(n + \frac{n^2}{m}\right)\omega_r t - 2\pi i(mn+n^2)} \quad (4)$$

$$= E_o e^{-i\omega_0(t+T)} \sum_n a_n e^{-i\left(n + \frac{n^2}{m}\right)\omega_r t}$$

$$= e^{-i2\pi m\omega_0/\omega_r} E(t)$$

The revival time is the m multiple of the cavity round trip group delay measured at the mode with n=0, i.e. at $\omega_0$.

Figure 3:
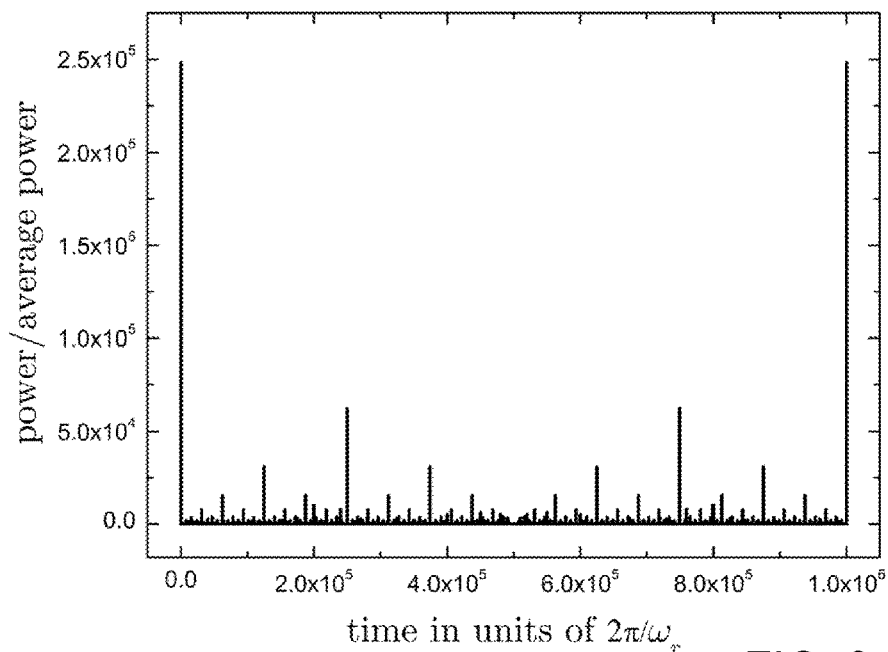
FIG. 3: an exemplary illustration of the temporal evolution of the light field amplitude of a periodic light field created in a resonator device according to the invention.

FIG. 3 shows an example of the time dependency of the power $\propto |E(t)|^2$ at a fixed point inside the laser cavity according to equation (3) normalized to the time averaged power. The recurrence coefficient is $m=10^6$, the carrier frequency $\omega_0 = 3 \times 10^6 \times \omega_r$ and the amplitudes follow a Gaussian distribution centered at $\omega_0$: $a_n = e^{-(n/1000,000)^2}$. After m cavity round trips the pulse reassembles with a peak power of the initial pulse. With these parameters the mode beatings equation (2) are separated by 200 Hz. Accordingly, like in a conventional mode locked laser, the peak power enhancement over the time averaged power is roughly given by the number of active modes. However, in contrast to the latter, the large peak power occurs not every cavity round trip but only every m-th cavity round trip. The usual Kerr lens mode locking mechanism might be used to enforce an integer m by reduced loss of the high peak intensity pulse.

In the case of the Talbot frequency comb, that large peak intensity occurs only every m-th round trip. Therefore, a strong self-amplitude modulation of the Kerr effect is used for successful mode locking.

To find the required dispersion that results in the mode spectrum, equation (1) is resolved for n:

$$n = \frac{m}{2}\left(\sqrt{1+4\frac{\omega_n - \omega_0}{m\omega_r}} - 1\right) \quad (5)$$

Like in any other laser with cavity length L, the round trip phase $\emptyset(w)$ at frequency $\omega$ has to fulfill the boundary condition:

$$\phi(\omega) = 2\pi n + \frac{L}{c}\omega_0 \quad (6)$$

$$= \pi m\left(\sqrt{1+4\frac{\omega - \omega_0}{m\omega_r}} - 1\right) + \frac{L}{c}\omega_0 \quad (7)$$

Since $\omega_0$ is the resonant mode with n=0, the last term has to be added to obtain the total round trip phase. Without loss of generality it is assumed in equation (1) that the parameter $\omega_0$ is the center of the emitted spectrum (see FIG. 5). Using equation (7) and computing the derivatives at $\omega_0$ the dispersion preferably provide for generating the mode spacing of equation (1) is obtained:

$$\phi''(\omega_0) = -\frac{4\pi}{m\omega_r^2} \quad (8)$$

$$\phi'''(\omega_0) = +\frac{24\pi}{m^2\omega_r^3} \quad (9)$$

$$\phi''''(\omega_0) = -\frac{240\pi}{m^3\omega_r^4} \ldots \quad (10)$$

$$\phi_{\omega_0}^{(k)} = (-1)^{k+1}\frac{2^k(2k-3)!!\pi}{m^{k-1}\omega_r^k} \quad (11)$$

Figure 5:
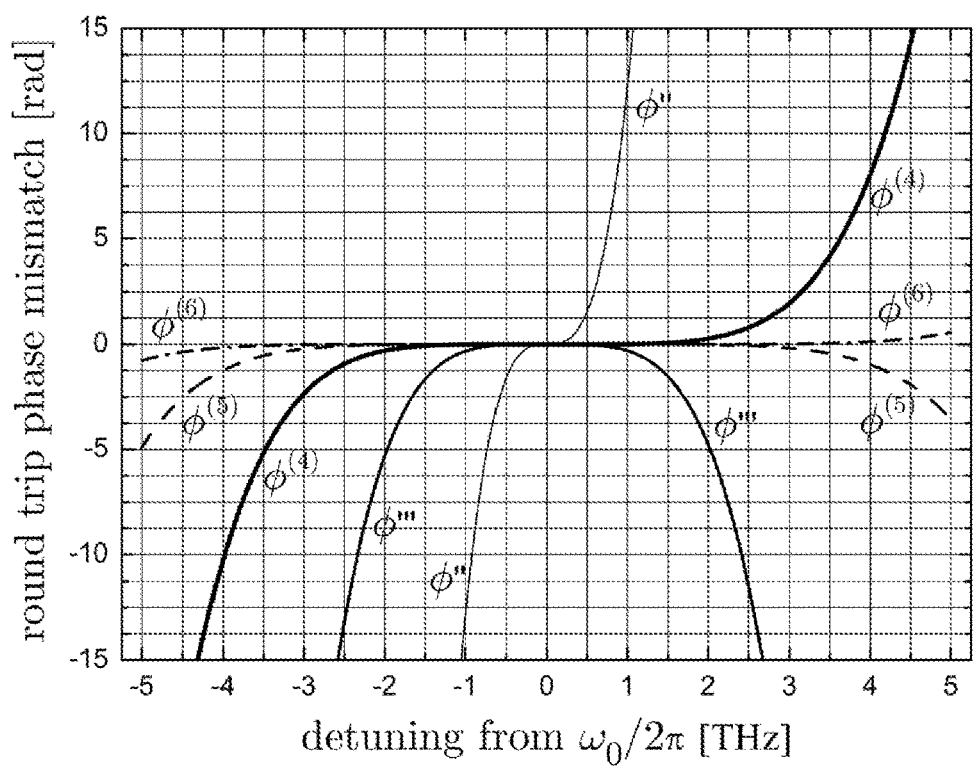
FIG. 5: a graphical illustration of the change of the spectral phase generating a periodic light field according to the invention.

For a practical laser pulse source apparatus 10, the requirements on the dispersion are quite extreme but not impossible (see FIGS. 1 and 5). These requirements are mitigated by large values of m, i.e. a long pulse revival time (for a given $\omega_r$). However this could lead to a reduced Kerr effect and hence weaken the mode locking mechanism. Once the laser is set up for a particular value of m, it will be reproduced every time it put in the mode locked condition.

With the example parameters of FIGS. 3 and 5 equation (11) provides $\phi''(\omega_0) = -3.2 \times 10^7 fs^2$, $\phi'''(\omega_0) = 3.0 \times 10^8 fs^3$, $\phi^4(\omega_0) = -4.8 \times 10^9 fs^4$ etc.

Rather than this expansion one might use the first term in equation (7) directly to compute the required dispersion. Besides that the FBG section 14 also compensates the higher order dispersion of the remaining components. To estimate the required length of the FBG section 14 for obtaining the required dispersion, the difference of the round trip phase delay for the two ends of the spectrum using equation (7) is calculated and the same difference of a cavity without dispersion is subtracted $\Delta\phi = \phi(\omega_0 + \Delta\omega/2) - \phi(\omega_0 - \Delta\omega/2)$ In this equation, $\Delta\omega$ is the spectral width of the spectral envelope of the laser pulses. This phase difference divided by $2\pi$ and multiplied by the carrier wavelength $\lambda = 2\pi c/\omega_0 = 1$ µm gives the path length difference that needs to be added for the two colors by the FBG section 14. Since the light travels twice through the FBGs section 14, the actual length is half this value. With the values m=$10^6$; $\omega_r = 2\pi*100$ MHz; $\omega_0 = 2\pi*300$ THz; $\Delta_\omega = 2\pi*10$ THz, e.g. $\Delta z = 4.2$ cm is obtained. The real length might then also depend on the requirements for the reflectivity. Fiber lasers generally come with a large optical gain so that it may be possible to compromise on that parameter. The design of the laser pulse source apparatus 10 could be a tradeoff between large m (=low dispersion) and small m (=stronger mode locking). To start operation at a very large value of m it may also conceivable to include an intracavity modulator that mimics all or parts of the temporal envelope shown in FIG. 3.

Figure 4:
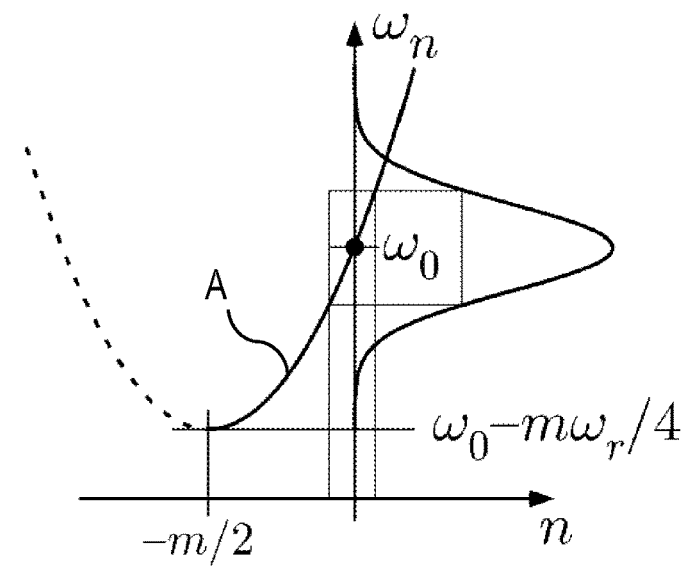
FIG. 4: a graphical illustration of frequencies of comb modes of a Talbot frequency comb created with the method of generating laser pulses according to the invention.

FIG. 4 represents frequencies of the modes of the Talbot frequency comb according to equation (1) shown as the curve A. The dashed part belongs to the negative mode spacing section (i.e. negative group velocity) not considered here.

Curve A defines the dispersion properties of the cavity whose expansion is shown in equation (11). The vertex of the curve at $[-m/2; \omega_0 - m\omega_r/4]$ and can be chosen without restriction by selecting m and $\omega_r$. The active modes, i.e. the laser spectrum, is assumed to be centered at $\omega_0$. It covers a certain range in $\omega_n$ and n-space (rectangular area). The curvature of the parabola reflects the required group velocity dispersion which can be minimized by large values of m and $\omega_r$ in accordance with equation (11).

FIG. 5 shows comparing the exact round trip phase given by equations (5) and (6) with the expansion given by equation (11) for different order with m=$10^6$ and $\omega_r = 2\pi \times 100$ MHz. With dispersion compensation up to $\phi^{(6)}(\omega)$, the phase mismatch increases to 0.77 rad at the edges of the spectrum (width 10 THz), i.e. about 0.12 free spectral ranges. This mismatch is compensated by the Kerr effect like in a conventional mode locked laser.

Self-Referencing of the Talbot Frequency Comb

For self-referencing the two parameters of the Talbot frequency comb $\omega_r$ and $\omega_0$ need to be measured and ideally stabilized. The recurrence index m is assumed to be known. One might get an estimate of it and then fix it to be an integer, by measuring the recurrence time and compare it to the cavity length. A more reliable method would be to measure a known optical frequency with a self-referenced Talbot frequency comb and then identify the proper m compatible with that measurement. This is the same method often applied with conventional frequency combs to determine the correct mode number.

The parameter $\omega_r$ can be determined by observing the mode beating dependence on n as expressed by equation (2), i.e. by the second order mode differences:

$$\frac{2}{m}\omega_r = \Delta_{n+1} - \Delta_n \quad (12)$$

In practical terms this frequency is readily generated by mixing of the RF modes and can then be locked to a precise reference frequency such as an atomic clock by feeding back on the cavity length and presumably also on the pump laser power. In that sense $\omega_r$ is determined almost as simple as the repetition rate of a regular frequency comb.

The second parameters of the Talbot comb, $\omega_0$ can be measured in very much the same way as done with the carrier envelope offset frequency of a regular comb [1], i.e. with an f-2f interferometer. A part from the red side of the Talbot comb with mode number $n_1$ is frequency doubled and superimposed the blue part of mode number $n_2$. According to equation (1) the generated beat notes have the frequencies:

$$2\omega_{n_1} - \omega_{n_2} = \omega_0 - \left(2n_2 - n_1 + \frac{2n_2^2 - n_1^2}{m}\right)\omega_r \quad (13)$$

The condition for a signal in the radio frequency domain is that out of the combinations of integers in the bracketed term there is one, that is large enough to multiply $\omega_r$ all the way up to the optical frequency $\omega_0$. For $m \to \infty$, this condition is identical of the comb spanning an optical octave. If the combs bandwidth is sufficient there many combinations of integers that fulfill this requirement, i.e. several radio frequency beat notes may be taken as $\omega_0$. Again this is very similar to regular frequency combs where the offset frequency is only determined modulo the repetition rate. Which of the beat notes is taken for $\omega_0$ does not matter as long as the mode numbering is adapted to that choice. Frequency doubling the Talbot comb however will generate even more frequencies as assumed in equation (13), as described with reference to FIG. 1.

The features of the invention disclosed in the above description, the drawings and the claims can be of significance individually, in combination or sub-combination for the implementation of the invention in its different embodiments.

The invention claimed is:

1. A method of generating laser pulses, comprising the steps of
    creating a circulating light field in a resonator device having a resonator length L and an intra-cavity dispersion and being configured for supporting a plurality of resonator modes of the light field, and
    generating a pulse train of the laser pulses by a mode-locking mechanism, wherein the laser pulses provide a frequency comb with a carrier frequency $\omega_o$ and plurality of comb modes in frequency space, wherein
    the intra-cavity dispersion is selected such that round trip phases $\phi$ have a dependency on frequency $\omega$ according to $$\phi(\omega) = \pi m\left(\sqrt{1 + 4\frac{\omega - \omega_0}{m\omega_r}} - 1\right) + \frac{L}{c}\omega_0$$

wherein m is an integer that gives an effective repetition rate $m\omega_r$ of the laser pulses in combination with a mode spacing $\omega_r$ at the optical carrier frequency $\omega_o$, and
    the mode-locking mechanism provides a coupling of the resonator modes such that a frequency difference ($\Delta_n = \omega_{n+1} - \omega_n$) between neighboring mode frequencies ($\omega_n$, $\omega_{n+1}$) is a linear function of an integer mode frequency number n.

2. The method according to claim 1, wherein the mode frequency $\omega_n$ with the mode frequency number n is given by $$\omega_n = \omega_0 + \left(n + \frac{n^2}{m}\right)\omega_r.$$

3. The method according to claim 2, wherein the intra-cavity dispersion is selected such that the k-th derivative of the comb mode phase at the carrier frequency $\omega_o$ is given by $$\phi_{\omega_0}^{(k)} = (-1)^{k+1}\frac{2^k(2k-3)!!\pi}{m^{k-1}\omega_r^k}$$

wherein k is the order of intra-cavity dispersion.

4. The method according to claim 1, wherein the frequency difference between neighboring comb frequencies ($\Delta_n = \omega_{n+1} - \omega_n$) is in a radio frequency range.

5. The method according to claim 1, wherein the intra-cavity dispersion is set with at least one fiber Bragg grating, at least one intracavity prism and/or at least one intracavity grating included in the resonator device.

6. The method according to claim 1, wherein the resonator device is a fiber ring laser.

7. A spectroscopy method for obtaining a spectral response of a sample, comprising the steps of
    generating a pulse train of laser pulses with a method according to claim 1,
    applying the laser pulses on the sample under investigation,
    detecting the laser pulses with a detector device,
    analyzing a detector signal of the detector device for obtaining beat signals created by the comb modes of the pulse train of laser pulses, and
    determining the spectral response of the sample from the beat signals.

8. The spectroscopy method according to claim 7, further comprising the steps of
    detecting a reference portion of the pulse train of laser pulses without an application on the sample with the detector device, and
    analyzing a reference detector signal of the detector device for obtaining reference beat signals created by the comb modes of the reference portion of the pulse train of laser pulses, wherein
    the spectral response of the sample is determined from the beat signals and the reference beat signals.

9. The spectroscopy method according to claim 7, wherein the detector device comprises at least one photodiode.

10. A laser pulse source apparatus, being configured for generating laser pulses, comprising
    a resonator device having a resonator length L and an intra-cavity dispersion and being configured for supporting a plurality of resonator modes of a circulating light field, and
    a mode-locking mechanism being arranged for generating the laser pulses providing a frequency comb with carrier frequency $\omega_o$ and a plurality of comb modes in frequency space, wherein the intra-cavity group velocity dispersion is selected such that round trip phases φ have a dependency on frequency ω according to $$\phi(\omega) = \pi m\left(\sqrt{1 + 4\frac{\omega - \omega_0}{m\omega_r}} - 1\right) + \frac{L}{c}\omega_0$$

wherein m is an integer that gives an effective repetition rate $m\omega_r$ of the laser pulses in combination with a mode spacing $\omega_r$ at the optical carrier frequency $\omega_o$, and the mode-locking mechanism is arranged for providing a coupling of the resonator modes such that the frequency difference ($\Delta_n = \omega_{n+1} - \omega_n$) between neighboring comb frequencies $\omega_n$, $\omega_{n+1}$ is a linear function of an integer mode frequency number n.

11. The laser pulse source apparatus according to claim 10, having at least one of the features the mode frequency ($\omega_n$) with the mode frequency number n is given by $$\omega_n = \omega_0 + \left(n + \frac{n^2}{m}\right)\omega_r,$$

the intra-cavity dispersion is selected such that the k-th derivative of the comb mode phase at the carrier frequency ($\omega_o$) is given by $$\phi^{(k)}_{\omega_0} = (-1)^{k+1} \frac{2^k(2k-3)!!\pi}{m^{k-1}\omega_r^k}$$

wherein k is the order of intra-cavity dispersion, and
the frequency difference between neighboring comb frequencies ($\Delta_n = \omega_{n+1} - \omega_n$) is included in a radio frequency range.

12. The laser pulse source apparatus according to claim 10, wherein the resonator device includes at least one fiber Bragg grating, at least one intracavity prism and/or at least one intracavity grating being arranged for setting the intra-cavity dispersion.

13. The laser pulse source apparatus according to claim 10, wherein the resonator device is a fiber ring laser.

14. A spectroscopy apparatus being configured for obtaining a spectral response of a sample under investigation, comprising
a laser pulse source apparatus according to claim 10,
a sample holder being configured for accommodating the sample and applying the laser pulses on the sample,
a detector device being configured for detecting the laser pulses,
a spectrum analyzer device being configured for analyzing a detector signal of the detector device for obtaining beat signals created by the comb modes of the pulse train of laser pulses, and
a calculation device being configured for determining the spectral response of the sample from the beat signals.

15. The spectroscopy apparatus according to claim 14, further comprising
a beam splitting device being arranged for directing a reference portion of the laser pulses without an application on the sample to the detector device, wherein
the spectrum analyzer device is configured for analyzing a reference detector signal of the detector device and for obtaining reference beat signals created by the comb modes of the reference portion of the pulse train of laser pulses, and
the calculation device is configured for determining the spectral response of the sample from the beat signals and the reference beat signals.

16. The spectroscopy apparatus according to claim 14, wherein the detector device comprises at least one photodiode.

* * * * *